(12) United States Patent
Lv et al.

(10) Patent No.: US 11,236,041 B2
(45) Date of Patent: Feb. 1, 2022

(54) TYPE-G CRYSTAL FORM OF FENOLAMINE, PREPARATION METHOD, COMPOSITION AND USE THEREOF

(71) Applicants: INSTITUTE OF MATARIA MEDICA, CHINESE ACADEMY OF MEDICAL SCIENCES, Bejing (CN); SHIJIAZHUANG YILING PHARMACEUTICAL CO., LTD., Shijiazhuang (CN)

(72) Inventors: Yang Lv, Hebei Province (CN); Shiying Yang, Hebei Province (CN); Gengtao Liu, Hebei Province (CN); Dan Zhang, Hebei Province (CN); Xiuqi Bao, Hebei Province (CN); Ping Xie, Hebei Province (CN)

(73) Assignees: INSTITUTE OF MATARIA MEDICA, CHINESE ACADEMY OF MEDICAL SCIENCES, Beijing (CN); SHIJIAZHUANG YILING PHARMACEUTICAL CO., LTD., Shijiazhuang (CN)

( * ) Notice: Subject to any disclaimer, the term of this patent is extended or adjusted under 35 U.S.C. 154(b) by 163 days.

(21) Appl. No.: 16/629,950

(22) PCT Filed: Sep. 7, 2018

(86) PCT No.: PCT/CN2018/104574
§ 371 (c)(1),
(2) Date: Jan. 9, 2020

(87) PCT Pub. No.: WO2019/011350
PCT Pub. Date: Jan. 17, 2019

(65) Prior Publication Data
US 2020/0157042 A1    May 21, 2020

(30) Foreign Application Priority Data
Jul. 11, 2017 (CN) .......................... 201710560703.3

(51) Int. Cl.
*C07C 233/22* (2006.01)
*A61K 9/20* (2006.01)
*A61K 9/48* (2006.01)

(52) U.S. Cl.
CPC .......... *C07C 233/22* (2013.01); *A61K 9/2009* (2013.01); *A61K 9/2013* (2013.01); *A61K 9/2018* (2013.01); *A61K 9/2054* (2013.01); *A61K 9/2059* (2013.01); *A61K 9/4858* (2013.01); *A61K 9/4866* (2013.01); *C07B 2200/13* (2013.01)

(58) Field of Classification Search
CPC .................................................. C07C 233/22
See application file for complete search history.

(56) References Cited

FOREIGN PATENT DOCUMENTS

| CN | 1445211 A | * | 10/2003 |
| CN | 1308288 C | | 4/2007 |
| WO | WO 2019/011349 A1 | | 1/2019 |

OTHER PUBLICATIONS

Swanson et al. Frontiers in Bioscience 2009, 14, 1642-1660 (Year: 2009).*
English Machine Translation of CN 1308288C, "New amide ramification of sweetsop as well as its preparing method, its medication composition and usage", 2007 (22 pages).
Chinese Search Report for CN 201710560703.3 dated Jul. 27, 2020.
Fang et al, "Protective effects of compound FLZ, a novel synthetic analogue of squamosamide, on B-amyloid-induced rat brain mitochondrial dysfunction in vitro," Acta Pharmacol Sin, May 2009, pp. 522-529.
First Chinese Office Action for CN 201710560703.3 dated Jul. 27, 2020.
Bao et al., "FLZ Attenuates a-Synuclein-lnduced Neurotoxicity by Activating Heat Shock Protein 70," Mol. Neurobiol., 13 pages (Jan. 7, 2016).
Bao et al., "Squamosamide Derivative FLZ Protected Tyrosine Hydroxylase Function in a Chronic MPTP/Probenecid Mouse Model of Parkinson's Disease," Naunyn-Schmiedeberg's Arch Pharmacol., vol. 388, pp. 549-556 (Feb. 13, 2015).
Bao et al., "The Novel Cyclic Squamosamide Derivative FLZ Improves Memory Deficits in Aged Mice and the Mechanisms," Chinese Journal of New Drugs, vol. 19, No. 10, pp. 867-872 (Dec. 31, 2010).

(Continued)

*Primary Examiner* — Matthew P Coughlin
(74) *Attorney, Agent, or Firm* — Foley & Lardner LLP

(57) ABSTRACT

The present invention discloses a type-G crystal form of fenolamine, a preparation method thereof, and a composition and use thereof. In particular, disclosed is a type-G crystal form of the fenolamine compound (chemical name: trans-2-(2,5-dimethoxyphenyl)-3-(4-hydroxy-3-methoxyphenyl)-N-(4-hydroxyphenylethyl)acrylamide, a preparation method thereof, and a composition and use thereof. Specifically, the present invention discloses the presence of a solid of a type-G fenolamine crystal form in solid state; a method for preparing the solid of type-G crystal form; and use of the solid of the type-G fenolamine crystal form as a pharmaceutical active ingredient in the manufacture of a medicament for prevention and treatment of Parkinson's disease (PD), improvement of learning and memory disorder, and treatment of memory loss and Alzheimer's disease (AD).

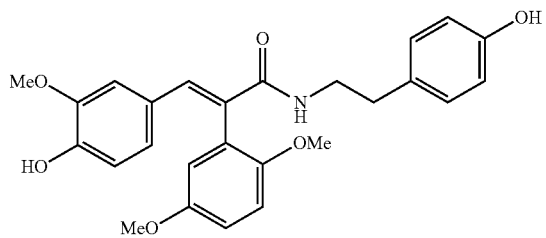

20 Claims, 4 Drawing Sheets

(56) References Cited

OTHER PUBLICATIONS

Cheng et al., "Squamosamide Derivative FLZ Protects Retinal Pigment Epithelium Cells from Oxidative Stress through Activation of Epidermal Growth Factor Receptor (EGFR)-AKT Signaling," Int. J. Mol. Sci., vol. 15, pp. 18762-18775 (Oct. 17, 2014).
Hou et al., "An In Vivo Microdialysis Study of FLZ Penetration through the Blood-Brain Barrier in Normal and 6-Hydroxydopamine Induced Parkinson's Disease Model Rats," BioMed Research International, 11 pages (Jun. 23, 2014).
Hou et al., "Quantitative determination and pharmacokinetic study of the novel anti-Parkinson's disease candidate drug FLZ in rat brain by high performance liquid chromatography—tandem mass spectrometry," Journal of Pharmaceutical and Biomedical Analysis, pp. 232-239 (Mar. 10, 2012).
International Search Report and Written Opinion, PCT/CN2018/104573 (dated Nov. 16, 2018) (WO 2019/011349-A1).
International Search Report and Written Opinion, PCT/CN2018/104574 (dated Nov. 28, 2018).
Ji et al., "Studies on Total Synthesis of Squamosamide," Acta Pharmaceutica Sinica, vol. 28, No. 6, pp. 428-431 (Dec. 31, 1993).
Liang-Yu Wu et al. FLZ attenuates learning and memory deficits via suppressing neuroinflammation induced by LPS in mice. Journal of Asian Natural Products Research, 2015,17(3): 306-317.
Li-bo Li et al. Establishment of a HPLC method for preclinical pharmacokinetic study of the novel anti-Parkinson's disease candidate drug FLZ in rats. Biomed. Chromatogr. 2008, 22: 867-872.
Qian Liu et al. P-Glycoprotein Mediated Efflux Limits the Transport of the Novel Anti-Parkinson's Disease Candidate Drug FLZ across the Physiological and PD Pathological In Vitro BBB Models. PLOS ONE, 2014, 9(7): e102442.
Technical guidelines for the dissolution test of common oral solid preparations.
Wenjiao Tai et al. Inhibition of Src tyrosine kinase activity by squamosamide derivative FLZ attenuates neuroinflammation in both in vivo and in vitro Parkinson's disease models. Neuropharmacology, 2013, 75: 201-212.
Xiang-chen Kong et al. FLZ, a novel HSP27 and HSP70 inducer, protects SH-SY5Y cells from apoptosis caused by MPP . Brain Research. 2011, 1383: 99-107.
Xiu-Qi Bao et al. Squamosamide derivative FLZ protected dopaminergic neuron by activating Akt signaling pathway in6-OHDA-induced in vivo and in vitro Parkinson0s disease models. Brain research, 2014, 1547: 49-57.
Xiu-Qi Bao, Ning Li et al. FLZ Alleviates the Memory Deficits in Transgenic Mouse Model of Alzheimer's Disease via Decreasing Beta-Amyloid Production and Tau Hyperphosphorylation. PLOS ONE, 2013, 8(11): e78033.
X-Q Bao et al. FLZ protects dopaminergic neuron through activating protein kinase B/mammalian target of rapamycin pathway and inhibiting RTP801 repression in Parkinson's disease models. Neuroscience. 2012, 202: 396-404.
Ye et al., "FLZ Inhibited Gamma-Secretase Selectively and Decreased Aß Mitochondrial Production in APP-SH-SY5Y Cells," Naunyn-Schmiedeberg's Arch Pharmacol., vol. 387, pp. 75-85 (Sep. 27, 2013).
Yong Qin et al. Anti-proliferative effects of the novel squamosamide derivative (FLZ) on HepG2 human hepatoma cells by regulating the cell cycle-related proteins are associated with decreased Ca2 /ROS levels. Chemico-Biological Interactions, 2011, 193: 246-253.
Zhang et al., "Squamosamide derivative FLZ protects dopaminergic neurons against inflammation-mediated neurodegeneration through the inhibition of NADPH oxidase activity," Journal of Neuroinflammation, 13 pages (May 28, 2008).
Zhang et al., "The novel squamosamide derivative (compound FLZ) attenuated 1-methyl, 4-phenyl-pyridinium ion (MPPt)-induced apoptosis and alternations of related signal transduction in SH-SY5Y cells," Neuropharmacology, pp. 423-429 (Aug. 2006).
Zhang et al., "The novel squamosamide derivative FLZ protects against 6-hydroxydopamine-induced apoptosis through inhibition of related signal transduction in SH-SY5Y cells," European Journal of Pharmacology, 6 pages (Nov. 16, 2006).

* cited by examiner

TYPE-G CRYSTAL FORM OF FENOLAMINE, PREPARATION METHOD, COMPOSITION AND USE THEREOF

CROSS-REFERENCE TO RELATED APPLICATIONS

This application is a National Stage Application of PCT/CN2018/104574, filed Sep. 7, 2018, which claims the benefit of and priority to Chinese Patent Application No. 201710560703.3, filed Jul. 11, 2017.

FIELD OF THE INVENTION

The present invention relates to the discovery of the presence of a solid state form of type-G crystal form of fenolamine in solid state, and to a method for preparing the type-G crystal form. The present invention relates to a pharmaceutical composition comprising the type-G crystal form of fenolamine and a mixed crystal form having any ratio of the type-G crystal form. The present invention also relates to use of the crystalline fenolamine species as a pharmaceutical active ingredient in the manufacture of a medicament for prevention and treatment of Parkinson's disease (PD), improvement of learning and memory disorder, and treatment of memory loss and Alzheimer's disease (AD).

BACKGROUND

The molecular structure of fenolamine (chemical name: trans-2-(2,5-dimethoxyphenyl)-3-(4-hydroxy-3-methoxyphenyl)-N-(4-hydroxyphenylethyl)-acrylamide) is:

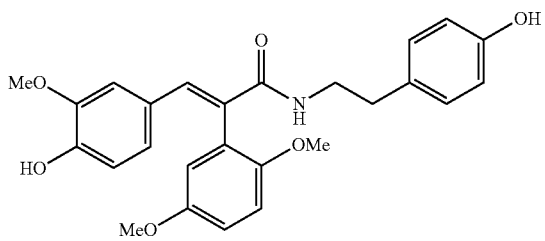 [SMILES: COc1ccc(OC)c(/C(=C\c2ccc(O)c(OC)c2)C(=O)NCCc2ccc(O)cc2)c1]

Fenolamine (FLZ) is a derivative of squamosamide, the compound structure of which has been disclosed in Chinese Patent Publication No. CN1445211 in which is described "new amide ramification of sweetsop as well as its preparing method, its medication composition and usage" invented by the Institute of Materia Medica, Chinese Academy of Medical Sciences[1]. Herein, Example 24 implicates a method for synthesizing fenolamine in which fenolamine is obtained by recrystallization from chloroform as solvent.

Seventeen articles concerning fenolamine were found upon literature search[2-19], but these articles all report on the pharmacological effects or pharmacokinetic studies of fenolamine, but do not involve preparation method and crystal form substance.

No patent or literature report on other crystal forms of fenolamine have been found by domestic and foreign patents and literature searches.

The inventors of present invention has discovered a new solid state of a type-G crystal form of fenolamine and a preparation method different from those reported in the above patents or literatures, determined the characteristics of changes in crystal forms in the blood and blood concentration after the solid of the type-G fenolamine crystal form is taken up by oral administration, and found that the solid of the type-G fenolamine crystal form has good stability.

The objective of the studies in the present invention is to seek and discover the species and state characteristics of crystalline solid substances at the level of raw materials for active ingredients of a medicament, by using crystal form screening techniques and crystal form biological activity evaluation techniques and starting from the study on the state of the present fenolamine crystalline solid, and associate the crystalline substances with pharmacodynamic studies, so as to provide fundamental scientific data for finding, discovering and developing a superior medicinal fenolamine crystalline solid having an optimal clinical efficacy; meanwhile, also to provide a scientific basis for seeking domestic or international patent protection of proprietary inventions based on the pharmaceutical raw material of the fenolamine solid.

SUMMARY OF THE INVENTION

A technical problem to be solved by the present invention is to provide fenolamine present in a new solid state and characterization means thereof, i.e., a type-G crystal form of fenolamine.

The second technical problem to be solved by the present invention is to provide a method for preparing a solid of the type-G fenolamine crystal form.

The third technical problem to be solved by the present invention is to provide a solid medicament containing a pure substance of fenolamine of the type-G crystal form or a mixed crystal form having any ratio of the type-G crystal form, and a composition thereof.

The fourth technical problem to be solved by the present invention is to provide a pharmaceutical composition having the solid of the type-G fenolamine crystal form as a pharmaceutically active ingredient in a daily dose of 10 to 3000 mg. The pharmaceutical composition includes a tablet, a capsule, a pill, an injection, a sustained release or a controlled release preparation.

The fifth technical problem to be solved by the present invention is to provide the use of the solid of the type-G fenolamine crystal form in the manufacture of a medicament for prevention and treatment of Parkinson's disease (PD), improvement of learning and memory disorder, and treatment of memory loss and Alzheimer's disease (AD).

In order to solve the above technical problems, the present invention adopts the following technical solutions:

1. Morphological Features of Fenolamine Type-G Crystal Form Samples 1.1 The present invention relates to a solid of a type-G fenolamine crystal form, wherein the solid of the type-G crystal form is a hydrate of fenolamine and, by using powder X-ray diffraction analysis under the $CuK_\alpha$ radiation experimental conditions, has diffraction peaks at positions with 2-Theta values (°) or d values (Å) and diffraction peaks with relative intensity peak height values (Height %) or peak area values (Area %) as shown in the following table (Table 1, FIG. 1).

TABLE 1

Powder X-ray diffraction peak values of fenolamine type-G crystal form samples

| Peak | 2-Theta ±0.2° | d (Å) ±0.2 Å | Height % ±10% | Area % ±10% |
|---|---|---|---|---|
| 1 | 7.3 | 12.2 | 20 | 29 |
| 2 | 7.8 | 11.4 | 15 | 18 |
| 3 | 9.2 | 9.6 | 10 | 11 |
| 4 | 10.7 | 8.2 | 21 | 23 |
| 5 | 11.3 | 7.8 | 34 | 58 |
| 6 | 11.6 | 7.6 | 29 | 48 |
| 7 | 12.6 | 7.0 | 7 | 8 |
| 8 | 13.1 | 6.7 | 47 | 64 |
| 9 | 13.6 | 6.5 | 13 | 18 |
| 10 | 15.0 | 5.9 | 10 | 11 |
| 11 | 15.6 | 5.7 | 5 | 4 |
| 12 | 17.6 | 5.0 | 33 | 45 |
| 13 | 18.3 | 4.8 | 70 | 72 |
| 14 | 19.6 | 4.5 | 37 | 57 |
| 15 | 19.9 | 4.5 | 41 | 76 |
| 16 | 20.4 | 4.3 | 78 | 84 |
| 17 | 20.8 | 4.3 | 21 | 30 |
| 18 | 22.1 | 4.0 | 16 | 15 |
| 19 | 22.7 | 3.9 | 4 | 2 |
| 20 | 23.4 | 3.8 | 100 | 100 |
| 21 | 23.9 | 3.7 | 12 | 14 |
| 22 | 24.7 | 3.6 | 51 | 45 |
| 23 | 25.5 | 3.5 | 69 | 82 |
| 24 | 26.5 | 3.4 | 6 | 6 |
| 25 | 27.2 | 3.3 | 9 | 10 |
| 26 | 27.9 | 3.2 | 7 | 6 |
| 27 | 28.6 | 3.1 | 12 | 13 |
| 28 | 29.1 | 3.1 | 12 | 19 |
| 29 | 30.5 | 2.9 | 8 | 9 |
| 30 | 31.5 | 2.8 | 5 | 5 |
| 31 | 32.9 | 2.7 | 6 | 14 |
| 32 | 33.9 | 2.6 | 3 | 4 |
| 33 | 34.3 | 2.6 | 3 | 5 |
| 34 | 34.9 | 2.6 | 1 | 1 |
| 35 | 35.6 | 2.5 | 4 | 6 |
| 36 | 37.3 | 2.4 | 3 | 3 |
| 37 | 38.1 | 2.4 | 6 | 8 |
| 38 | 40.1 | 2.2 | 4 | 8 |
| 39 | 41.5 | 2.2 | 2 | 2 |
| 40 | 42.3 | 2.1 | 6 | 5 |

1.2 The present invention relates to a solid of a type-G fenolamine crystal form, wherein the solid of the type-G crystal form contains a hydrated water component, and it shows one weight loss peak in the range of 40 to 150° C. with a weight loss of 3.0% to 5.0% by using thermogravimetric analysis (FIG. 2) and has a water content of 3.0% to 5.0% by using Karl Fischer moisture analysis.

1.3 The present invention relates to a solid of a type-G fenolamine crystal form, wherein by using differential scanning calorimetry analysis, one endothermic peak is present at a temperature of 96° C.±3° C. in the DSC spectrum in a range of 30 to 150° C. and at a heating rate of 3° C. per minute (FIG. 3).

1.4 The present invention relates to a solid of a type-G fenolamine crystal form, wherein by using attenuated total reflection Fourier infrared spectroscopy analysis, IR characteristic peaks are present at 3375, 2937, 2836, 1643, 1591, 1580, 1525, 1509, 1498, 1466, 1453, 1425, 1412, 1370, 1261, 1220, 1181, 1166, 1121, 1071, 1042, 1033, 1019, 944, 923, 895, 851, 817, 788, 774, 755, 732, 711, and 693 $cm^{-1}$, wherein the allowable deviation of the IR characteristic peaks is ±2 $cm^{-1}$ (FIG. 4).

1.5 A solid of mixed fenolamine crystal forms comprising the solid of a type-G fenolamine crystal form according to any one of the present invention at any non-zero ratio.

2. Features in Preparation of Type-G Fenolamine Crystal Form Samples and Mixed Crystal 2.1 The present invention relates to a method for preparing a type-B fenolamine solid, wherein the solid of a type-G fenolamine crystal form is prepared by suspending a fenolamine solid material in water and stirring for 1 to 24 hours at an ambient temperature of 4° C. to 80° C. and an ambient humidity of 10% to 80% under normal pressure, and drying by suction filtration under reduced pressure for 1 to 24 hours.

2.2 The solid of mixed fenolamine crystal forms of the present invention is obtained by mixing the type-G fenolamine crystal form component prepared by the above method with solid of other fenolamine crystal forms in an arbitrary ratio by a conventional method.

3. Pharmaceutical Composition Containing a Component of Fenolamine Crystal Form(s), Dosing Regimen Features and Pharmaceutical Use 3.1 The present invention relates to a pharmaceutical composition which comprises a type-G fenolamine crystal form and a pharmaceutically acceptable carrier.

3.2 The present invention relates to a pharmaceutical composition which comprises a solid of mixed fenolamine crystal forms and a pharmaceutically acceptable carrier.

3.3 The present invention relates to a pharmaceutical composition having a daily dose of fenolamine in the range of 10 to 3000 mg.

3.4 The present invention relates to a pharmaceutical composition, wherein the pharmaceutical composition is various tablets, capsules, pills, powder injection, sustained release preparations or controlled release preparations, and is in a solid dosage form.

3.5 The present invention relates to the use of type-G fenolamine crystal form in the manufacture of a medicament for prevention and treatment of Parkinson's disease (PD), improvement of learning and memory disorders, and treatment of memory loss and Alzheimer's disease (AD).

3.6 The present invention relates to the use of a solid of mixed fenolamine crystal forms comprising the type-G fenolamine crystal form at any ratio in the manufacture of a medicament for prevention and treatment of Parkinson's disease (PD), improvement of learning and memory disorders, and treatment of memory loss and Alzheimer's disease (AD).

The present invention relates to the use of a pharmaceutical composition in the manufacture of a medicament for prevention and treatment of Parkinson's disease (PD), improvement of learning and memory disorders, and treatment of memory loss and Alzheimer's disease (AD).

The present invention relates to a pharmaceutical composition comprising the type-G fenolamine crystal form component of the present invention or the solid of mixed fenolamine crystal forms of the present invention as an active ingredient. The pharmaceutical composition can be prepared according to methods well known in the art. The type-G fenolamine crystal form component of the present invention or the solid of mixed fenolamine crystal forms of the present invention can be prepared into any dosage forms suitable for human or animal use by combining with one or more pharmaceutically acceptable solid or liquid excipients and/or adjuvants. The content of the type-G fenolamine crystal form component of the present invention or the solid of mixed fenolamine crystal forms of the present invention is usually from 0.1 to 95% by weight in the pharmaceutical composition.

The type-G fenolamine crystal form component of the present invention or the solid of mixed fenolamine crystal forms of the present invention, or a pharmaceutical composition containing the same may be administered in a unit dosage form. The route of administration may be an enteral or parenteral route, such as oral, intravenous, intramuscular, subcutaneous, nasal, oral mucosa, ocular, lung and respiratory, skin, vaginal, rectal route, and the like.

The dosage form in which the present invention is administered is preferably a solid dosage form. The solid dosage form may be a tablet (including common tablet, enteric tablet, buccal tablet, dispersible tablet, chewable tablet, effervescent tablet, orally disintegrating tablet), a capsule (including hard capsule, soft capsule, enteric capsule), a granule, a powder, a pellet, a dropping pill, a suppository, a film, a patch, a gas (powder) spray, a spray, and the like.

The type-G fenolamine crystal form component of the present invention or the solid of mixed fenolamine crystal forms of the present invention can be prepared into a common preparation, a sustained release preparation, a controlled release preparation, a targeting preparation, and various microparticle delivery systems.

In order to formulate the type-G fenolamine crystal form component of the present invention or the solid of mixed fenolamine crystal forms of the present invention into a tablet, various excipients known in the art, including diluents, binders, wetting agents, disintegrants, lubricants, glidants, can be broadly used. The diluent may be starch, dextrin, sucrose, glucose, lactose, mannitol, sorbitol, xylitol, microcrystalline cellulose, calcium sulfate, calcium hydrogen phosphate, calcium carbonate and the like; the wetting agent may be water, ethanol, isopropanol or the like; the binder may be starch syrup, dextrin, syrup, honey, glucose solution, microcrystalline cellulose, gum arabic, gelatin syrup, sodium carboxymethyl cellulose, methyl cellulose, hydroxypropyl methyl cellulose, ethyl cellulose, acrylic resin, carbomer, polyvinylpyrrolidone, polyethylene glycol or the like; the disintegrant may be dry starch, microcrystalline cellulose, low-substituted hydroxypropyl cellulose, cross-linked polyvinylpyrrolidone, croscarmellose sodium, sodium carboxymethyl starch, sodium hydrogencarbonate and citric acid, polyoxyethylene sorbitan fatty acid ester, sodium dodecyl sulfate or the like; the lubricant and glidant can be talc, silica, stearate, tartaric acid, liquid paraffin, polyethylene glycol or the like.

Tablets may also be further formed into coated tablets, such as sugar coated tablets, film coated tablets, enteric coated tablets, or bilayer tablets and multi-layer tablets.

In order to prepare the dosage unit into a capsule, the active ingredient of type-G fenolamine crystal form component of the present invention or the solid of mixed fenolamine crystal forms of the present invention may be blended with a diluent or a glidant, and the mixture may be placed directly into a hard capsule or a soft capsule. Alternatively, the active ingredient of the type-G fenolamine crystal form component of the present invention or the solid of mixed fenolamine crystal forms of the present invention and a diluent, a binder, or a disintegrant may be first granulated or pelletized, and then placed into a hard capsule or a soft capsule. Various diluents, binders, wetting agents, disintegrants, and glidant materials for preparing the tablets of the type-G fenolamine crystal form component of the present invention or the solid of mixed fenolamine crystal forms of the present invention can also be used for preparing the capsules of the type-G fenolamine crystal form component of the present invention or the solid of mixed fenolamine crystal forms of the present invention.

In addition, colorants, preservatives, perfumes, flavoring agents, or other additives may also be added to the pharmaceutical preparations, if necessary.

The medicament or pharmaceutical composition of the present invention can be administered by any known administration method for the purpose of the administration and enhancing therapeutic effects.

The dosage of the pharmaceutical composition of the type-G fenolamine crystal form component of the present invention or the solid of mixed fenolamine crystal forms of the present invention may vary widely depending on the nature and severity of the disease to be prevented or treated, the individual conditions of the patient or animal, the route of administration and the dosage form and the like. The above dosages may be administered in one dosage unit or in separate dosage units depending on the clinical expertise of the physician and the dosage regimen including the use of other therapeutic means.

The type-G fenolamine crystal form component of the present invention or the solid of mixed fenolamine crystal forms of the present invention or the composition can be administered alone or in combination with other therapeutic drugs or symptomatic drugs. When there is a synergistic effect of the type-G fenolamine crystal form component of the present invention or the solid of mixed fenolamine crystal forms of the present invention and other therapeutic agents, the dosage thereof should be adjusted according to the actual situation.

4. Advantageous Technical Effects of the Present Invention 4.1 Stability of Type-G Fenolamine Crystal Form:

The solid of the type-G fenolamine crystal form of the present invention has good stability. Influencing factor experimental results show that the solid of the type-G fenolamine crystal form is stable under conditions of high temperature, high humidity and light.

4.2 Safety of Type-G Fenolamine Crystal Form:

The solid of type-G fenolamine crystal form the present invention does not contain any toxic and harmful crystallization solvent but only hydrated water, and is advantageous in safe formulation of medicaments.

DETAILED DESCRIPTION OF THE INVENTION

The technical solutions of the present invention are described in details below with reference to the accompanying drawings and examples. However, the scope of protection of the present invention includes these embodiments but is not limited thereto.

Example 1

Figure 1:
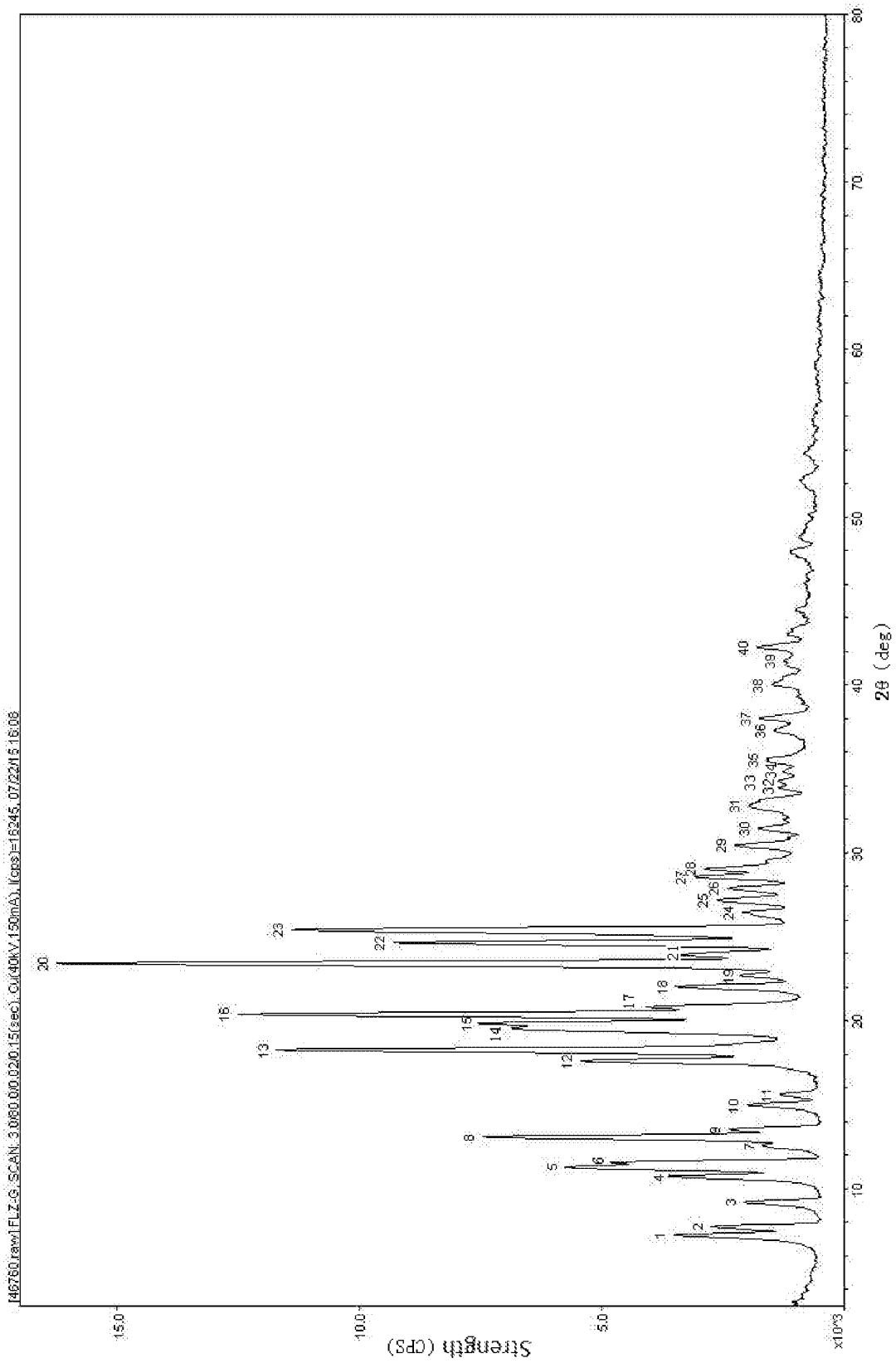
FIG. 1 is a powder X-ray diffraction pattern of a type-G fenolamine crystal form sample.
Figure 2:
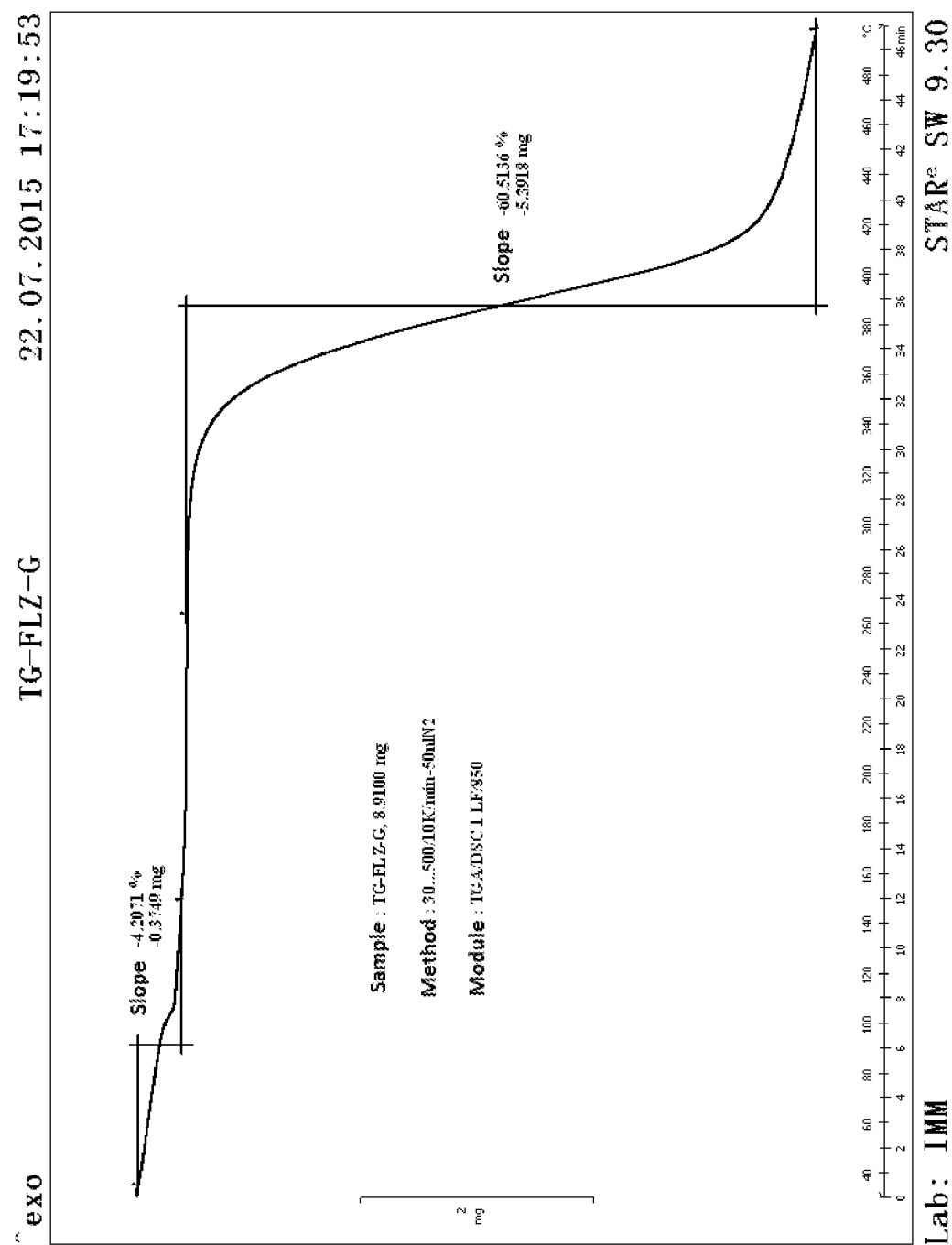
FIG. 2 is a TG diagram of a type-G fenolamine crystal form sample.
Figure 3:
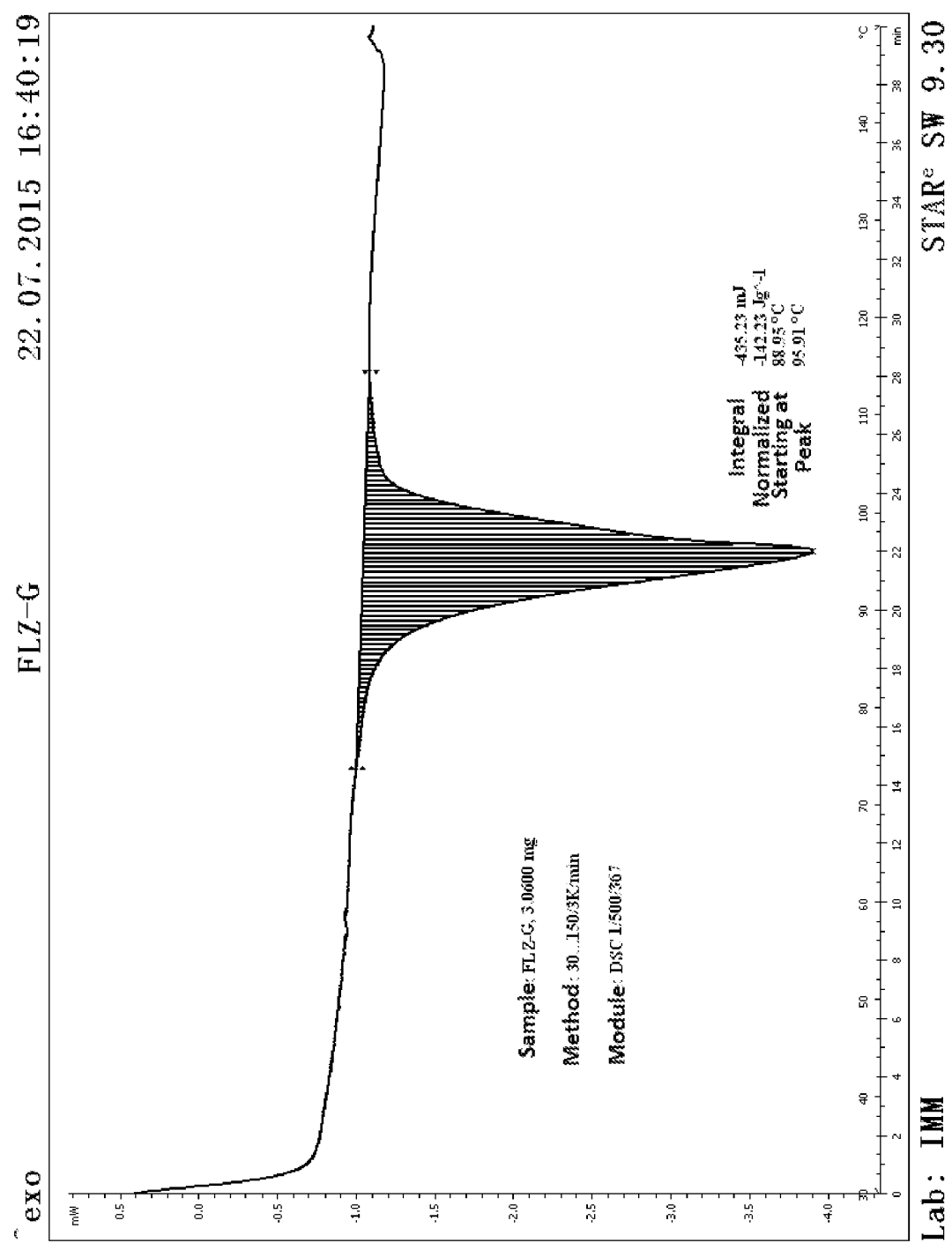
FIG. 3 is a DSC profile of a type-G fenolamine crystal form sample.
Figure 4:
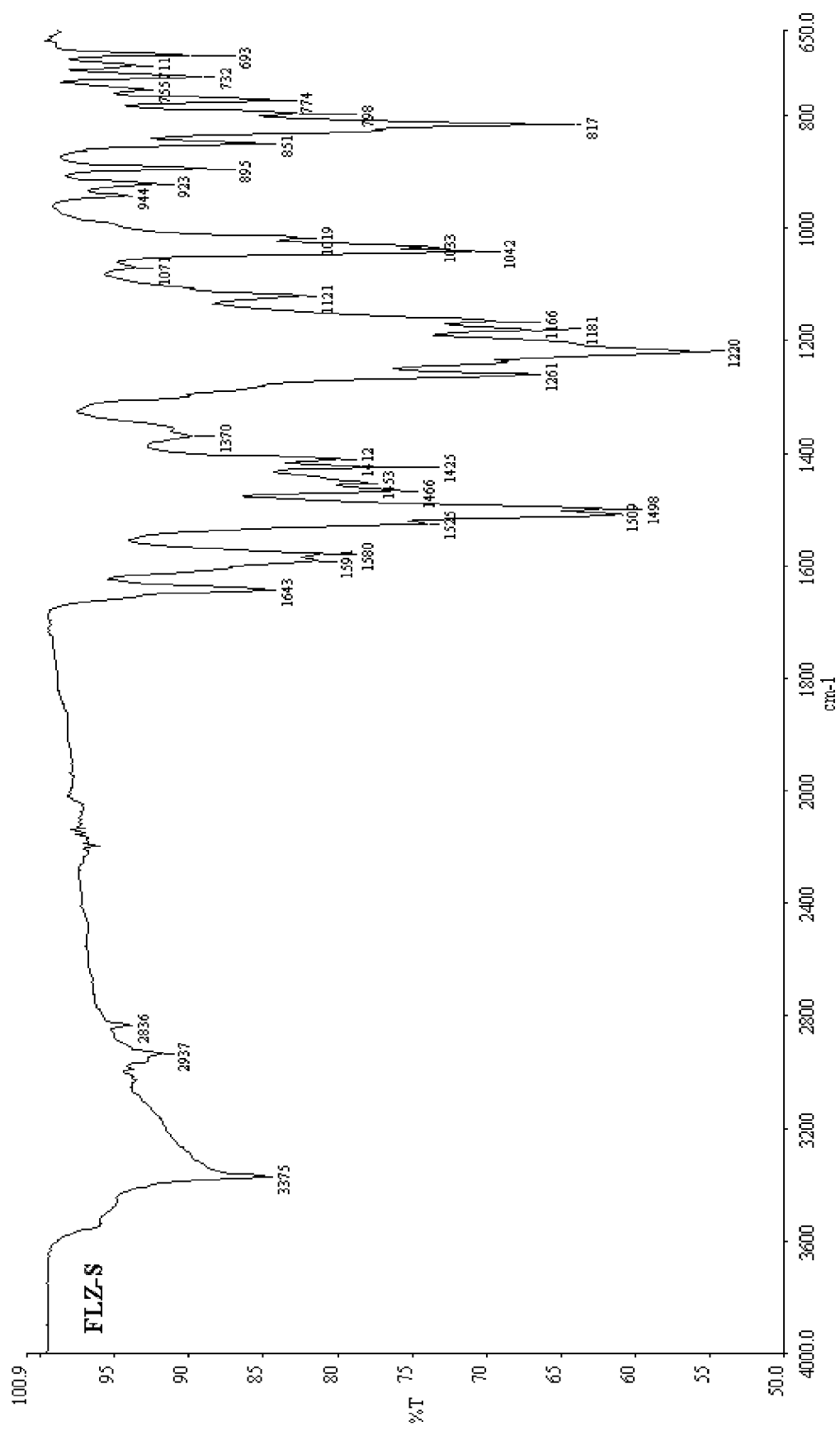
FIG. 4 is an infrared absorption spectrum of a type-G fenolamine crystal form sample.

Preparation Method 1 of Type-G Fenolamine Crystal Form Sample:

0.5 g of a solid sample of fenolamine recrystallized from ethanol as solvent was added to 50 mL of distilled water, placed under conditions of a constant temperature of 40° C. and an ambient humidity of 30%, stirred at a constant rate for 6 hours, filtered, and dried under reduced pressure for 2 hours to obtain a solid sample. Powder X-ray diffraction analysis (FIG. 1) shows that the obtained sample is a solid of a type-G crystal form, and the thermogravimetric diagram, DSC profile, and infrared spectrum are shown in FIG. 2 to FIG. 4.

Preparation Method 2 of Type-G Fenolamine Crystal Form Sample:

0.5 g of a solid sample of fenolamine recrystallized from acetone as solvent was added to 100 mL of distilled water, placed under conditions of a constant temperature of 50° C. and an ambient humidity of 50%, stirred at a constant rate for 3 hours, filtered, and dried under reduced pressure for 4 hours to obtain a solid sample. Powder X-ray diffraction analysis gives a pattern consistent to that of FIG. 1, and the thermogravimetric diagram, DSC profile, and infrared spectrum are consistent with those shown in FIG. 2 to FIG. 4, indicating that the obtained sample is a solid of a type-G crystal form.

Preparation Method 3 of Type-G Fenolamine Crystal Form Sample:

0.5 g of a solid sample of fenolamine recrystallized from isopropanol as solvent was added to 40 mL of distilled water, placed under conditions of a constant temperature of 60° C. and an ambient humidity of 40%, stirred at a constant rate for 8 hours, filtered, and dried under reduced pressure for 8 hours to obtain a solid sample. Powder X-ray diffraction analysis gives a pattern consistent to that of FIG. 1, and the thermogravimetric diagram, DSC profile, and infrared spectrum are consistent with those shown in FIG. 2 to FIG. 4, indicating that the obtained sample is a solid of a type-G crystal form.

Preparation Method 4 of Type-G Fenolamine Crystal Form Sample:

0.5 g of a solid sample of fenolamine recrystallized from chloroform as solvent was added to 80 mL of distilled water, placed under conditions of a constant temperature of 60° C. and an ambient humidity of 40%, stirred at a constant rate for 5 hours, filtered, and dried under reduced pressure for 12 hours to obtain a solid sample. Powder X-ray diffraction analysis gives a pattern consistent to that of FIG. 1, and the thermogravimetric diagram, DSC profile, and infrared spectrum are consistent with those shown in FIG. 2 to FIG. 4, indicating that the obtained sample is a solid of a type-G crystal form.

Preparation Method 5 of Type-G Fenolamine Crystal Form Sample:

0.5 g of a solid sample of fenolamine recrystallized from ethyl acetate as solvent was added to 100 mL of distilled water, placed under conditions of a constant temperature of 50° C. and an ambient humidity of 40%, stirred at a constant rate for 2 hours, filtered, and dried under reduced pressure for 6 hours to obtain a solid sample. Powder X-ray diffraction analysis gives a pattern consistent to that of FIG. 1, and the thermogravimetric diagram, DSC profile, and infrared spectrum are consistent with those shown in FIG. 2 to FIG. 4, indicating that the obtained sample is a solid of a type-G crystal form.

Preparation Method 6 of Type-G Fenolamine Crystal Form Sample:

0.5 g of a solid sample of amorphous fenolamine was added to 150 mL of distilled water, placed under conditions of a constant temperature of 50° C. and an ambient humidity of 40%, stirred at a constant rate for 10 hours, filtered, and dried under reduced pressure for 24 hours to obtain a solid sample. Powder X-ray diffraction analysis gives a pattern consistent to that of FIG. 1, and the thermogravimetric diagram, DSC profile, and infrared spectrum are consistent with those shown in FIG. 2 to FIG. 4, indicating that the obtained sample is a solid of a type-G crystal form.

Example 2

Stability of Solid of Type-G Fenolamine Crystal Form:

Type-G fenolamine crystal form samples were placed in open clean watch glasses, and kept under conditions of a high temperature of 60° C., a high temperature of 40° C., and 25° C., a relative humidity of 90%±5%, and illumination at 4500 lx±500 lx for 10 days, and samples were taken on Days 0, 5, and 10. Powder X-ray diffraction (with a resultant pattern consistent to that in FIG. 1) and gas chromatography means were used for analysis. The results show that the type-G fenolamine crystal form is stable under conditions of high temperature, high humidity and light illumination, indicating that the solid of the type-G crystal form has good stability. All of the products from Example 1 were subjected to this test and achieved the same effect.

Example 3

Preparation Method 1 of Combinational Drug Preparation (Tablet):

A preparation method of a combinational drug tablet is characterized in that a pure product of type-G fenolamine crystal form or a solid of mixed crystal forms containing any ratio of the type-G crystal form used as a pharmaceutical raw material for a combinational drug, together with several excipients as adjuvant ingredients for preparing a combinational drug tablet, are used and formulated in a certain ratio into a tablet sample containing 50 to 500 mg drug per tablet. Table 2 shows the proportions in the tablet formulation:

TABLE 2

Formulations for preparing fenolamine combinational drug tablets

| | Amount in Formulation | | | | | | |
|---|---|---|---|---|---|---|---|
| Names of raw materials and excipients | Formulation 1 | Formulation 2 | Formulation 3 | Formulation 4 | Formulation 5 | Formulation 6 | Formulation 7 |
| Fenolamine (mg) | 50.0 | 75.0 | 100.0 | 150.0 | 250.0 | 300.0 | 500.0 |
| Lactose (mg) | q.s. | q.s. | q.s. | q.s. | q.s. | q.s. | q.s. |
| Starch (mg) | q.s. | q.s. | q.s. | q.s. | q.s. | q.s. | q.s. |

TABLE 2-continued

Formulations for preparing fenolamine combinational drug tablets

| Names of raw materials and excipients | Amount in Formulation | | | | | | |
|---|---|---|---|---|---|---|---|
| | Formulation 1 | Formulation 2 | Formulation 3 | Formulation 4 | Formulation 5 | Formulation 6 | Formulation 7 |
| Low substituted hydroxypropyl cellulose (mg) | q.s. | q.s. | q.s. | q.s. | q.s. | q.s. | q.s. |
| Microcrystalline cellulose (mg) | q.s. | q.s. | q.s. | q.s. | q.s. | q.s. | q.s. |
| Talc powder (mg) | q.s. | q.s. | q.s. | q.s. | q.s. | q.s. | q.s. |
| Magnesium stearate (mg) | q.s. | q.s. | q.s. | q.s. | q.s. | q.s. | q.s. |
| 1% sodium hydroxymethyl-cellulose (mg) | q.s. | q.s. | q.s. | q.s. | q.s. | q.s. | q.s. | q.s.: appropriate amount

The process of formulating a pure product of type-G fenolamine crystal form or a solid of mixed crystal forms containing any ratio of the type-G crystal form as a pharmaceutical raw material into a tablet preparation includes: uniformly mixing several excipients and the pharmaceutical raw material, adding an appropriate amount of a 1% sodium carboxymethylcellulose solution to prepare a soft material, sieving and granulating, drying the wet granules, sieving the granules, adding magnesium stearate and talc powder before mixing evenly, and pressing to obtain the tablets.

Preparation Method 2 of Combinational Drug Preparation (Capsule):

A preparation method of a combinational drug capsule is characterized in that a pure product of type-G fenolamine crystal form or a solid of mixed crystal forms containing any ratio of the type-G crystal form used as a pharmaceutical raw material for a combinational drug, together with several excipients as adjuvant ingredients for preparing a combinational drug capsule, are used and formulated in a certain ratio into a capsule sample containing 50 to 500 mg drug per tablet. Table 3 shows the proportions in the capsule formulation:

TABLE 3

Formulations of raw materials and excipients for preparing fenolamine combinational drug capsules

| Names of raw materials and excipients | Amount in Formulation | | | | | | |
|---|---|---|---|---|---|---|---|
| | Formulation 1 | Formulation 2 | Formulation 3 | Formulation 4 | Formulation 5 | Formulation 6 | Formulation 7 |
| Fenolamine (mg) | 50.0 | 75.0 | 100.0 | 150.0 | 250.0 | 300.0 | 500.0 |
| Lactose (mg) | q.s. | q.s. | q.s. | q.s. | q.s. | q.s. | q.s. |
| Starch (mg) | q.s. | q.s. | q.s. | q.s. | q.s. | q.s. | q.s. |
| Microcrystalline cellulose (mg) | q.s. | q.s. | q.s. | q.s. | q.s. | q.s. | q.s. |
| Magnesium stearate (mg) | q.s. | q.s. | q.s. | q.s. | q.s. | q.s. | q.s. |
| 1% sodium hydroxymethyl-cellulose (mg) | q.s. | q.s. | q.s. | q.s. | q.s. | q.s. | q.s. | q.s.: appropriate amount

The process of formulating a pure product of type-G fenolamine crystal form or a solid of mixed crystal forms containing any ratio of the type-G crystal form as a pharmaceutical raw material into a tablet preparation includes: uniformly mixing several excipients and the pharmaceutical raw material, adding an appropriate amount of a 1% sodium carboxymethylcellulose solution and granulating to prepare wet granules, drying and sieving the granules, adding magnesium stearate before uniformly mixing, and incorporating into a capsule. Alternatively, without the granulating step, the type-G fenolamine crystal form raw material is directly mixed with several excipients uniformly, and sieved and incorporated directly into a capsule.

Example 4

Dosage 1 for Administration of a Crystalline Fenolamine Combinational Drug (Tablet):

A pharmaceutical composition is developed and prepared by using a crystalline fenolamine sample as a pharmaceutically active ingredient, characterized in that the type-G fenolamine crystal form is used as a pharmaceutically active ingredient with a daily dose of 10 to 3000 mg, and can be prepared to be given in 1 to 6 common tablets each containing 10, 100, 200, 300, or 500 mg of the active ingredient once or twice per day, respectively.

Dosage 2 for Administration of a Crystalline Fenolamine Combinational Drug (Capsule):

A pharmaceutical composition is developed and prepared by using a crystalline fenolamine sample as a pharmaceutically active ingredient, characterized in that the type-G fenolamine crystal form is used as a pharmaceutically active ingredient with a daily dose of 10 to 3000 mg, and can be prepared to be given in 1 to 6 capsules each containing 10, 100, 200, 300, or 500 mg of the active ingredient once or twice per day, respectively.

It is noteworthy that there are many factors influencing the given dosage of the active ingredient in the crystalline fenolamine pharmaceutical composition of the present invention, for example, different daily doses resulted from different preventative or therapeutic uses; different daily doses resulted from differences in the nature of the disease and the severity of the disease; different daily doses resulted from differences in gender, age, and body surface area of the patient, the route of administration, the number of administrations, and the purpose of treatment. In addition, the absorption and blood concentration of the crystalline sample may also vary, resulting in a suitable daily dosage in the range of 0.01 to 300 mg/kg body weight, preferably 1 to 50 mg/kg body weight, for using the crystalline fenolamine component according to the present invention. According to the actual needs in the prevention and treatment of various conditions in use, different overall dosage regimens may be established which can be accomplished by giving the active ingredient of the type-G fenolamine crystal form once or several times.

The invention claimed is:

1. A solid of a type-G fenolamine crystal form, wherein the solid of the type-G crystal form is a fenolamine hydrate and, by using powder X-ray diffraction analysis under CuKα radiation experimental conditions, has diffraction peaks at positions with 2-Theta values or d values and diffraction peaks with relative intensity peak height values or peak area values as shown below:

| Peak | 2-Theta ±0.2° | d (Å) ±0.2 Å | Height % ±10% | Area % ±10% |
|---|---|---|---|---|
| 1 | 7.3 | 12.2 | 20 | 29 |
| 2 | 7.8 | 11.4 | 15 | 18 |
| 3 | 9.2 | 9.6 | 10 | 11 |
| 4 | 10.7 | 8.2 | 21 | 23 |
| 5 | 11.3 | 7.8 | 34 | 58 |
| 6 | 11.6 | 7.6 | 29 | 48 |
| 7 | 12.6 | 7.0 | 7 | 8 |
| 8 | 13.1 | 6.7 | 47 | 64 |
| 9 | 13.6 | 6.5 | 13 | 18 |
| 10 | 15.0 | 5.9 | 10 | 11 |
| 11 | 15.6 | 5.7 | 5 | 4 |
| 12 | 17.6 | 5.0 | 33 | 45 |
| 13 | 18.3 | 4.8 | 70 | 72 |
| 14 | 19.6 | 4.5 | 37 | 57 |
| 15 | 19.9 | 4.5 | 41 | 76 |
| 16 | 20.4 | 4.3 | 78 | 84 |
| 17 | 20.8 | 4.3 | 21 | 30 |
| 18 | 22.1 | 4.0 | 16 | 15 |
| 19 | 22.7 | 3.9 | 4 | 2 |
| 20 | 23.4 | 3.8 | 100 | 100 |
| 21 | 23.9 | 3.7 | 12 | 14 |
| 22 | 24.7 | 3.6 | 51 | 45 |
| 23 | 25.5 | 3.5 | 69 | 82 |
| 24 | 26.5 | 3.4 | 6 | 6 |
| 25 | 27.2 | 3.3 | 9 | 10 |
| 26 | 27.9 | 3.2 | 7 | 6 |
| 27 | 28.6 | 3.1 | 12 | 13 |
| 28 | 29.1 | 3.1 | 12 | 19 |
| 29 | 30.5 | 2.9 | 8 | 9 |
| 30 | 31.5 | 2.8 | 5 | 5 |
| 31 | 32.9 | 2.7 | 6 | 14 |
| 32 | 33.9 | 2.6 | 3 | 4 |
| 33 | 34.3 | 2.6 | 3 | 5 |
| 34 | 34.9 | 2.6 | 1 | 1 |
| 35 | 35.6 | 2.5 | 4 | 6 |
| 36 | 37.3 | 2.4 | 3 | 3 |
| 37 | 38.1 | 2.4 | 6 | 8 |
| 38 | 40.1 | 2.2 | 4 | 8 |
| 39 | 41.5 | 2.2 | 2 | 2 |
| 40 | 42.3 | 2.1 | 6 | 5 |

2. The solid of a type-G fenolamine crystal form according to claim 1, wherein the solid of the type-G crystal form contains a hydrated water component, and it shows one weight loss peak in the range of 40 to 150° C. with a weight loss of 3.0% to 5.0% by using thermogravimetric analysis and has a water content of 3.0% to 5.0% by using Karl Fischer moisture analysis.

3. The solid of a type-G fenolamine crystal form according to claim 1, wherein by using differential scanning calorimetry analysis, one endothermic peak is present at a temperature of 96° C.±3° C. in a DSC spectrum in a range of 30 to 150° C. and at a heating rate of 3° C. per minute.

4. The solid of a type-G fenolamine crystal form according to claim 1, wherein by using attenuated total reflection Fourier infrared spectroscopy analysis, IR characteristic peaks are present at 3375, 2937, 2836, 1643, 1591, 1580, 1525, 1509, 1498, 1466, 1453, 1425, 1412, 1370, 1261, 1220, 1181, 1166, 1121, 1071, 1042, 1033, 1019, 944, 923, 895, 851, 817, 788, 774, 755, 732, 711, and 693 cm$^{-1}$, wherein the allowable deviation of the IR characteristic peaks is ±2 cm$^{-1}$.

5. The solid of a type-G fenolamine crystal form according to claim 1, wherein the solid of the type-G fenolamine crystal form is prepared by suspending a fenolamine solid material in water and stirring for 1 to 24 hours at an ambient temperature of 4° C. to 80° C. and an ambient humidity of 10% to 80% under normal pressure, and drying by suction filtration under reduced pressure for 1 to 24 hours.

6. A pharmaceutical composition comprising from 0.1 to 95 wt. % of a solid of mixed fenolamine crystal forms comprising the solid of a type-G fenolamine crystal form according to claim 1.

7. A pharmaceutical composition comprising an effective amount of the solid of type-G fenolamine crystal form according to claim 1, and a pharmaceutically acceptable carrier.

8. The pharmaceutical composition according to claim 7 comprising an amount of a solid of mixed fenolamine crystal forms comprising the solid of a type-G fenolamine crystal form according to claim 1 in the range of 10 to 500 mg.

9. The pharmaceutical composition according to claim 7, wherein the pharmaceutical composition is in a dosage form of a tablet, a capsule, a pill, a powder for injection, a sustained release preparation, or a controlled release preparation, and is in a solid dosage form.

10. A pharmaceutical composition comprising from 0.1 to 95 wt. % of a solid of a mixed fenolamine crystal forms comprising the solid of a type-G fenolamine crystal form according to claim 2.

11. A pharmaceutical composition comprising from 0.1 to 95 wt. % of a solid of a mixed fenolamine crystal forms comprising the solid of a type-G fenolamine crystal form according to claim 3.

12. A pharmaceutical composition comprising from 0.1 to 95 wt. % of a solid of a mixed fenolamine crystal forms comprising the solid of a type-G fenolamine crystal form according to claim 5.

13. A pharmaceutical composition comprising an effective amount of the solid of mixed fenolamine crystal forms according to claim 6 and a pharmaceutically acceptable carrier.

14. The pharmaceutical composition according to claim 13 comprising an amount of a solid of mixed fenolamine crystal forms comprising the solid of a type-G fenolamine crystal form according to claim 1 in the range of 10 to 500 mg.

15. The pharmaceutical composition according to claim 13, wherein the pharmaceutical composition is in a dosage form of a tablet, a capsule, a pill, a powder for injection, a sustained release preparation, or a controlled release preparation, and is in a solid dosage form.

16. A method of treating Parkinson's disease, improving learning and memory disorders, and treating memory loss and Alzheimer's disease comprising administering to a patient or animal in need thereof an effective amount of the solid of a fenolamine crystal form according to claim 1.

17. A method of treating Parkinson's disease, improving learning and memory disorders, and treating memory loss and Alzheimer's disease comprising administering to a patient or animal in need thereof the pharmaceutical composition according to claim 6 comprising an effective amount of the solid of mixed fenolamine crystal forms.

18. A method of treating Parkinson's disease, improving learning and memory disorders, and treating memory loss and Alzheimer's disease comprising administering to a patient or animal in need thereof an effective amount of the pharmaceutical composition according to claim 7.

19. A pharmaceutical composition comprising from 0.1 to 95 wt. % of a solid of a mixed fenolamine crystal forms comprising the solid of a type-G fenolamine crystal form according to claim 4.

20. A method of treating Parkinson's disease, improving learning and memory disorders, and treating memory loss and Alzheimer's disease comprising administering to a patient or animal in need thereof the pharmaceutical composition according to claim 19 comprising an effective amount of the solid of mixed fenolamine crystal forms.

\* \* \* \* \*